United States Patent
Ishida et al.

(10) Patent No.: US 8,603,310 B2
(45) Date of Patent: Dec. 10, 2013

(54) GAS-CONCENTRATION/HUMIDITY DETECTION APPARATUS

(75) Inventors: Noboru Ishida, Kakamigahara (JP); Kentaro Mori, Nagoya (JP); Tomohiro Tajima, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 6 days.

(21) Appl. No.: 13/147,988

(22) PCT Filed: Apr. 19, 2010

(86) PCT No.: PCT/JP2010/002808
§ 371 (c)(1),
(2), (4) Date: Aug. 4, 2011

(87) PCT Pub. No.: WO2010/140293
PCT Pub. Date: Dec. 9, 2010

(65) Prior Publication Data
US 2011/0290015 A1  Dec. 1, 2011

(30) Foreign Application Priority Data

Jun. 5, 2009  (JP) .................................. 2009-136184

(51) Int. Cl.
*G01N 27/409* (2006.01)
*G01N 27/41* (2006.01)

(52) U.S. Cl.
USPC ........... 204/406; 204/410; 204/411; 204/425; 73/29.01; 123/703

(58) Field of Classification Search
USPC ................ 204/400–401, 406–407, 409–412, 204/415–416, 418–421, 424–433, 435; 73/23.31, 23.32, 29.01; 205/780.5, 205/781, 782–784.5, 785.5–787, 793; 123/703
See application file for complete search history.

(56) References Cited

U.S. PATENT DOCUMENTS

| | | | |
|---|---|---|---|
| 4,851,103 A | 7/1989 | Usami et al. | |
| 6,375,828 B2 | 4/2002 | Ando et al. | |
| 6,743,352 B2 | 6/2004 | Ando et al. | |
| 6,923,902 B2 | 8/2005 | Ando et al. | |
| 2002/0017467 A1 | 2/2002 | Ando et al. | |
| 2002/0130053 A1 | 9/2002 | Ando et al. | |
| 2003/0042151 A1 | 3/2003 | Ando et al. | |
| 2009/0084677 A1* | 4/2009 | Kawase et al. | 204/402 |
| 2011/0132340 A1* | 6/2011 | Soltis | 123/703 |

FOREIGN PATENT DOCUMENTS

| | | |
|---|---|---|
| JP | 62-002149 A | 1/1987 |
| JP | 62-150151 A | 7/1987 |
| JP | 63-085351 A | 4/1988 |
| JP | 6-265516 A | 9/1994 |
| JP | 10-267885 A | 10/1998 |
| JP | 11-148910 A | 6/1999 |

* cited by examiner

*Primary Examiner* — Susan D Leong
(74) *Attorney, Agent, or Firm* — Sughrue Mion, PLLC

(57) ABSTRACT

A sensor control apparatus (3) includes a full-range gas sensor composed of an oxygen concentration detection cell having a pair of electrodes (21, 22) and an oxygen pump cell having a pair of electrodes (19, 20). In an electric circuit section (30), an Ip current flowing between the electrodes (19, 20) is controlled such that an electromotive force Vs produced between the electrodes (21, 22) becomes equal to a reference voltage. The reference voltage is usually set to a first reference voltage. However, when the subject gas is air, the reference voltage is set to a second reference voltage. Humidity of the subject gas is detected on the basis of an error $\Delta Ip$ between an Ip current detected when the reference voltage is set to the first reference voltage, and an Ip current detected when the reference voltage is set to the second reference voltage.

4 Claims, 6 Drawing Sheets

GAS-CONCENTRATION/HUMIDITY DETECTION APPARATUS

CROSS REFERENCE TO RELATED APPLICATION

This application is a National Stage of International Application No. PCT/JP2010/002808, filed Apr. 19, 2010, claiming priority based on Japanese Patent Application No. 2009-136184, filed Jun. 5, 2009, the contents of all of which are incorporated herein by reference in their entirety.

TECHNICAL FIELD

The present invention relates to a gas-concentration/humidity detection apparatus which detects humidity of air, introduced as a subject gas (gas to be detected), by use of a gas sensor for detecting the gas concentration of a specific component of the subject gas.

BACKGROUND ART

One of sensors conventionally used in automobiles is an oxygen sensor which is disposed in an exhaust passage of an internal combustion engine (automotive engine) so as to detect the concentration of oxygen contained in exhaust gas. This oxygen sensor detects not only the oxygen concentration of exhaust gas but also the air-fuel ratio of exhaust gas, by making use of a phenomenon that the magnitude of current flowing through a sensor element changes in accordance with the oxygen concentration of exhaust gas. A sensor control apparatus that controls drive of this oxygen sensor has a function of controlling the supply of electricity to the sensor element, converting current flowing through the sensor element to a voltage, and outputting the voltage to an electronic control unit (ECU). The ECU obtains the oxygen concentration and/or air-fuel ratio of exhaust gas on the basis of an output from the sensor control apparatus. In the ECU, the obtained oxygen concentration and/or air-fuel ratio of exhaust gas is utilized for air-fuel ratio feedback control such as adjustment of fuel injection amount.

An oxygen sensor mounted on an automobile has a possibility of its output shifting under a given condition if the characteristic of the sensor changes as a result of, for example, deterioration with time or deterioration of permanent properties. Therefore, there has been known a technique of correcting a change in the characteristic of an oxygen sensor on the basis of a sensor output in an air. For example, there has been disclosed an exhaust gas concentration detection method and an apparatus therefor in which air is supplied to a gas sensor, and the zero point of the detection output of the gas sensor is calibrated on the basis of the detection output of the gas sensor exposed to air (for example, see Patent Document 1). Further, there has been disclosed an air-fuel-ratio detection apparatus which detects the humidity of air, corrects an atmospheric condition output in accordance with the humidity, and employs the corrected output as an air calibration value, which accurately corresponds to the oxygen partial pressure of air, whereby the sensor characteristic is corrected accurately (for example, see Patent Document 2).

PRIOR ART DOCUMENTS

Patent Documents

Patent Document 1: Japanese Patent Application Laid-Open (kokai) No. H11-148910

Patent Document 2: Japanese Patent Application Laid-Open (kokai) No. S62-2149

SUMMARY OF THE INVENTION

Problems to be Solved by the Invention

However, an oxygen sensor exposed to air has a possibility of its output under a given condition changing due to influence of humidity of air. For example, in the case where the humidity of air is high, the oxygen partial pressure of air is low as compared with the case where the humidity of air is low. Therefore, the number of oxygen molecules detected by the oxygen sensor decreases substantially, and the sensor output tends to decrease.

Specifically, as shown in FIGS. 8 and 9, an Ip value (here, called an "air Ip value") detected by an oxygen sensor exposed to air tends to decrease when the humidity of air is high, as compared with the case where the humidity of air is low. Notably, FIG. 8 exemplifies the air IP value detected under the condition of air temperature being "30° C." for a low humidity state (relative humidity: 0%) and for a high humidity state (relative humidity: 80%). In the low humidity state (relative humidity: 0%), since air has a gas composition (volume ratio) such that the volume ratio of nitrogen ($N_2$) is "80" and the volume ratio of oxygen ($O_2$) is "20," the oxygen concentration of air becomes "20%." Meanwhile, in the high humidity state (relative humidity: 80%), if air has a gas composition (volume ratio) such that the volume ratio of nitrogen ($N_2$) is "80," the volume ratio of oxygen ($O_2$) is "20," and the volume ratio of moisture ($H_2O$) is "1.95," the oxygen concentration of air becomes "19.6%." Because of a difference in oxygen partial pressure of air, in the high humidity state, for example, "3.854 mA" is detected as the air IP value; and, in the low humidity state, for example, "3.777 mA" is detected as the air IP value. That is, the detected air IP value has an error $\Delta Ip$ (here about "2.0%") in accordance with the humidity of air to which the oxygen sensor is exposed.

Therefore, even in the case where a change in the characteristic of an oxygen sensor is corrected on the basis of a sensor output in air, if the humidity at the time of detection of oxygen concentration differs from that at the time of correction, the detection accuracy of the sensor may drop because of the humidity difference. Also, in the case of the air-fuel-ratio detection apparatus described in Patent Document 2, since a humidity sensor is separately provided so as to detect the humidity of air, the structure of the apparatus becomes complex, which may increase manufacturing cost.

The present invention has been accomplished so as to solve the above-described problems, and an object of the present invention is to provide a gas-concentration/humidity detection apparatus which can accurately detect humidity of air, introduced as a subject gas, through employment of a simple structure using a gas sensor for detecting the concentration of a specific component of the subject gas (hereinafter the concentration of the specific component may be referred to as the "gas concentration").

Means for Solving the Problems

Application Example 1

A gas-concentration/humidity detection apparatus according to one mode of the present invention includes a gas sensor connected thereto and detecting concentration of a specific component of a subject gas and humidity of air introduced into the gas sensor as the subject gas, wherein the gas sensor comprises an oxygen concentration detection cell which includes a first solid electrolyte body and a pair of first electrodes formed on the first solid electrolyte body, one of the first electrodes being disposed within a detection chamber into which the subject gas is introduced, and the other first electrode being exposed to an oxygen concentration atmosphere serving as a reference; and an oxygen pump cell which includes a second solid electrolyte body and a pair of second electrodes formed on the second solid electrolyte body, one of the second electrodes being disposed within the detection chamber, and which pumps out oxygen contained in the subject gas introduced into the detection chamber or pumps oxygen into the detection chamber in accordance with current flowing between the pair of second electrodes. The gas-concentration/humidity detection apparatus comprises current control means for detecting a voltage produced between the pair of first electrodes due to a difference between an oxygen concentration within the detection chamber and an oxygen concentration within the oxygen reference chamber and for controlling the current flowing between the pair of second electrodes such that the voltage produced between the pair of first electrodes becomes equal to a control target voltage; atmosphere determination means for determining whether or not the subject gas is air; voltage setting means for setting the control target voltage to a first voltage and for setting the control target voltage to a second voltage greater than the first voltage when the atmosphere determination means determines that the subject gas is air; first current detection means for detecting a first current which flows between the pair of second electrodes in a state in which the first voltage is produced between the pair of first electrodes; second current detection means for detecting a second current which flows between the pair of second electrodes in a state in which the second voltage is produced between the pair of first electrodes; and humidity detection means for detecting humidity of the subject gas on the basis of the first current detected by the first current detection means when the atmosphere determination means determines that the subject gas is air, and the second current detected by the second current detection means after the first voltage is changed to the second voltage by the voltage setting means.

Notably, preferably, of the first and second voltages set as the control target voltage, the first voltage is set within a range in which moisture within the subject gas introduced into the gas detection chamber does not dissociate substantially, and the second voltage is set within a range in which the moisture within the subject gas introduced into the gas detection chamber dissociates.

Application Example 2

The gas-concentration/humidity detection apparatus according to the one mode of the present invention may comprise gas concentration detection means for detecting the concentration of the specific component on the basis of the first current detected by the first current detection means; and correction value determination means for determining a correction value, which is used for correcting the concentration detected by the gas concentration detection means, on the basis the humidity detected by the humidity detection means and the first current detected by the first current detection means when the atmosphere determination means determines that the subject gas is air.

Application Example 3

In the gas-concentration/humidity detection apparatus according to the one mode of the present invention, the humidity detection means may obtain the humidity on the basis of a difference obtained by subtracting the first current from the second current.

Application Example 4

In the gas-concentration/humidity detection apparatus according to the one mode of the present invention, the humidity detection means may detect the humidity on the basis of the first current detected by the first current detection means immediately before the control target voltage is set to the second voltage.

Effects of the Invention

The gas-concentration/humidity detection apparatus of Application example 1 includes a gas sensor composed of an oxygen concentration detection cell having a pair of first electrodes, and an oxygen pump cell having a pair of second electrodes. Current flowing between the pair of second electrodes is controlled such that a voltage produced between the pair of first electrodes becomes equal to a control target voltage. The control target voltage is usually set to a first voltage. However, when the subject gas is air, the control target voltage is set to a second voltage. Humidity of the subject gas is detected on the basis of first and second currents detected when the subject gas is determined to be air. Thus, it becomes possible to detect the humidity of air, introduced as the subject gas, through employment of a simple structure using a gas sensor for detecting the concentration of a specific component of the subject gas, without separately providing a humidity sensor.

According to the gas-concentration/humidity detection apparatus of Application example 2, by means of correcting the gas concentration by use of a correction value, the influence of moisture contained in the subject gas can be removed from the detected gas concentration, whereby the detection accuracy of the sensor output can be improved.

According to the gas-concentration/humidity detection apparatus of Application example 3, the humidity of air introduced as the subject gas can be detected accurately through simple processing of obtaining the difference between the first current and the second current.

According to the gas-concentration/humidity detection apparatus of Application example 4, the time difference between the detection timing of the first current and that of the second current can be reduced so as to suppress the occurrence of a problem in that the humidity changes between the detection of the first current and the detection of the second current.

MODES FOR CARRYING OUT THE INVENTION

An embodiment of a gas-concentration/humidity detection apparatus according to the present invention will next be described with reference to the drawings. In the present embodiment, a sensor control apparatus 3—which can detect the oxygen concentration of a subject gas and the humidity of air introduced as the subject gas, on the basis of a detection signal output by a gas sensor—will be described as an example of the gas-concentration/humidity detection apparatus according to the present invention. In the present embodiment, the gas sensor is a full-range air-fuel-ratio sensor 1 whose current (sensor current) changes linearly in accordance with the oxygen concentration.

Figure 1:
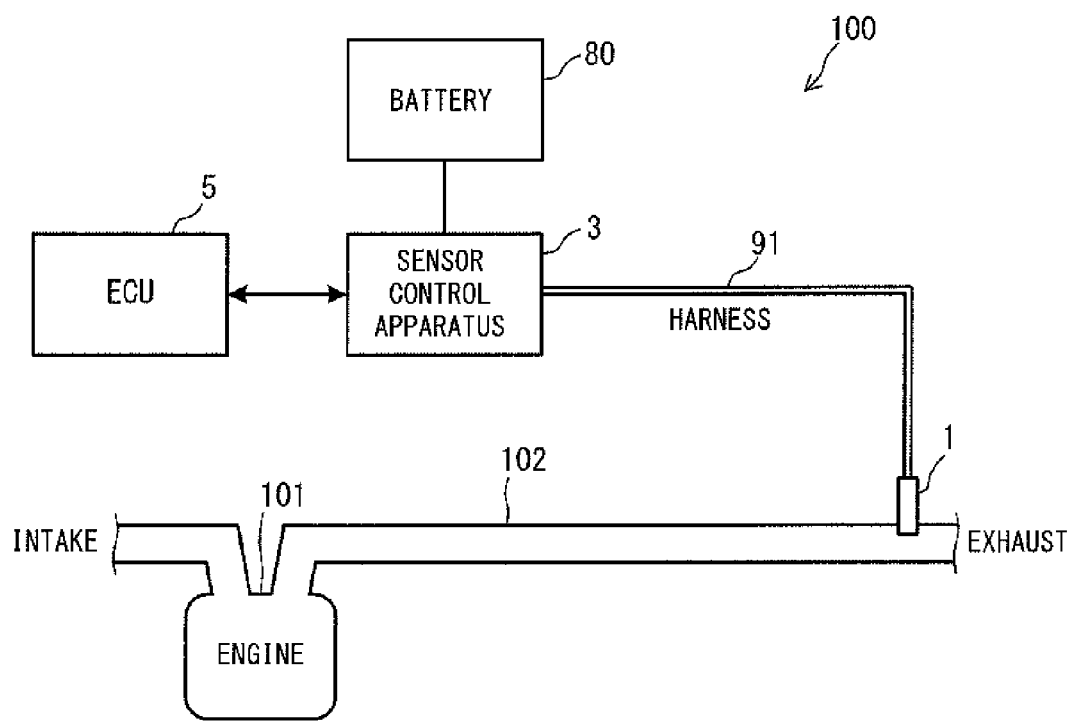
FIG. 1 Diagram schematically showing the configuration of an exhaust system of an internal combustion engine system 100.

First, the structure of an internal combustion engine system 100, to which the sensor control apparatus 3 is attached, will be briefly described with reference to FIG. 1. The internal combustion engine system 100 includes an engine 101 for propelling an automobile. An exhaust pipe 102 is connected to the engine 101 so as to discharge to the outside of the automobile exhaust gas discharged from the engine 101. The full-range air-fuel-ratio sensor 1 is disposed in an exhaust passage formed by the exhaust pipe 102. More specifically, the full-range air-fuel-ratio sensor 1 is a gas sensor for detecting the concentration of a specific component (oxygen in the present embodiment) contained in exhaust gas flowing through the exhaust passage formed by the exhaust pipe 102. The full-range air-fuel-ratio sensor 1 is connected, via a harness (signal wire) 91, to the sensor control apparatus 3, which is disposed at a position separated away from the sensor. The sensor control apparatus 3 energizes and controls the full-range air-fuel-ratio sensor 1 so as to detect the oxygen concentration. The sensor control apparatus 3 operates upon receipt of electric power from a battery 80, and outputs to an engine control unit (ECU) 5 a detection signal which represents the oxygen concentration detected by use of the full-range air-fuel-ratio sensor 1. In ECU 5, air-fuel-ratio feedback control is performed for the engine 101 on the basis of the output of the full-range air-fuel-ratio sensor 1.

In the present embodiment, when fuel is supplied to the engine 101, exhaust gas as described above is to be a subject gas detected by the full-range air-fuel-ratio sensor 1. Meanwhile, in a state in which the supply of fuel to the engine 101 is stopped (in fuel cut periods), since air flows through the exhaust pipe 102, the air flowing through the exhaust pipe 102 is to be a subject gas detected by the full-range air-fuel-ratio sensor 1. In the following description, the term "subject gas" which represents a gas exposed to the full-range air-fuel-ratio sensor 1 encompasses exhaust gas and air.

Figure 2:
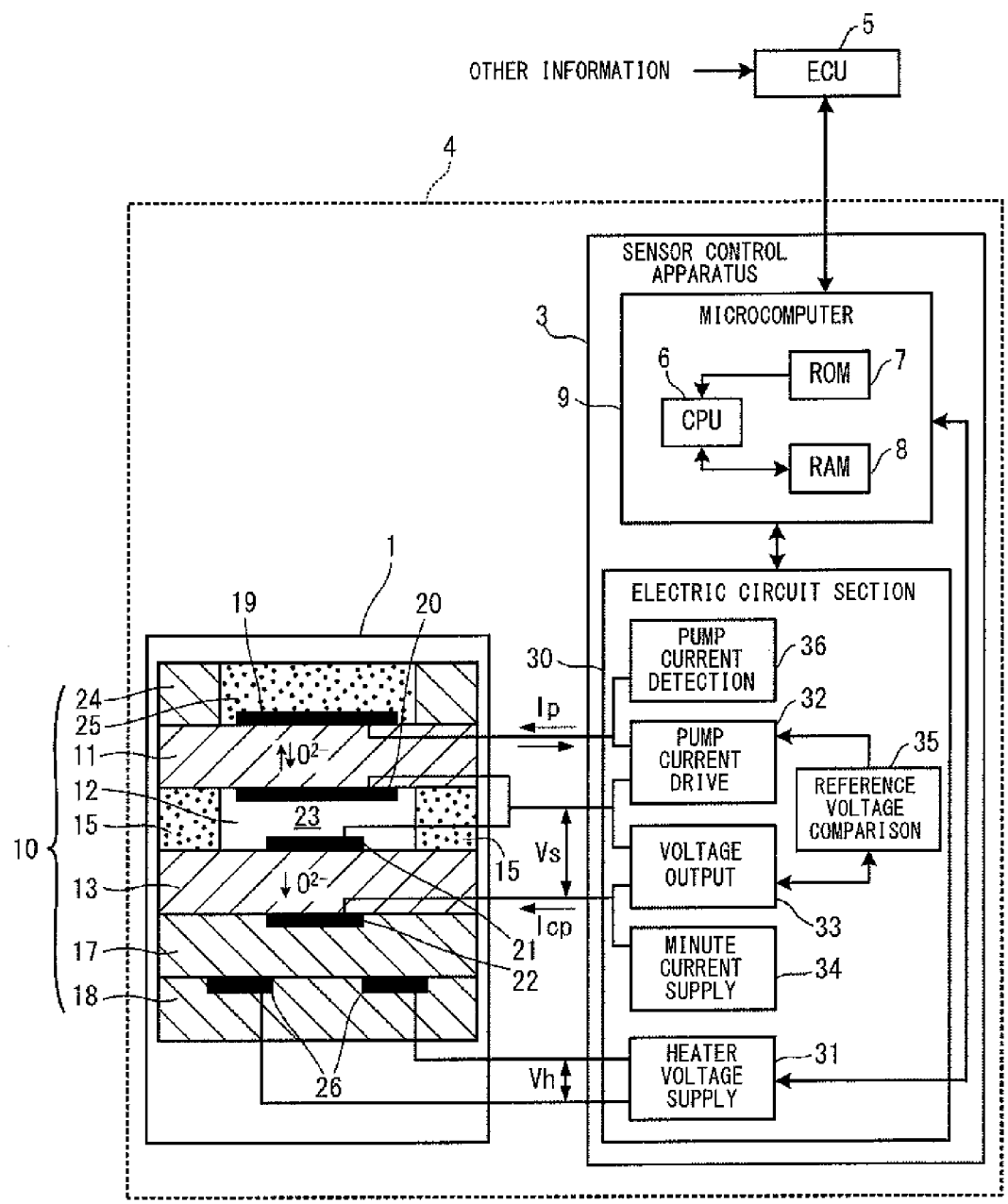
FIG. 2 Diagram schematically showing the structure of a full-range air-fuel-ratio sensor 1.

Next, with reference to FIG. 2, the full-range air-fuel-ratio sensor 1 and the sensor control apparatus 3 will be described in detail. The full-range air-fuel-ratio sensor 1 includes a sensor element 10 assuming the form of an elongated long plate, and an unillustrated housing which holds the sensor element 10 therein. The full-range air-fuel-ratio sensor 1 is electrically connected to the sensor control apparatus 3, which is disposed at a position remote from the full-range air-fuel-ratio sensor 1, via the harness 91 for taking out the output signal of the sensor element 10.

Notably, the present embodiment exemplifies the case where the sensor control apparatus 3 is provided between the full-range air-fuel-ratio sensor 1 and the ECU 5, and the full-range air-fuel-ratio sensor 1 and the sensor control apparatus 3 constitute a sensor unit 4. The "gas-concentration/humidity detection apparatus" in the present invention corresponds to the sensor control apparatus 3 connected to the full-range air-fuel-ratio sensor 1 (that is, the sensor unit 4). Needless to say, the manner of disposing the sensor control apparatus 3 can be changed freely. For example, the sensor control apparatus 3 may be incorporated into the ECU 5. In this case, the full-range air-fuel-ratio sensor 1 and the ECU 5 may constitute a sensor unit.

First, the structure of the sensor element 10 will be described. The sensor element 10 has a structure in which solid electrolyte bodies 11 and 13 mainly formed of zirconia, and insulating substrates 12, 17, 18, and 24 mainly formed of alumina are stacked in the order of the insulating substrate 18, the insulating substrate 17 the solid electrolyte body 13, the insulating substrate 12, the solid electrolyte body 11, and the insulating substrate 24. Paired electrodes 19 and 20 mainly formed of platinum are formed on opposite sides of the solid electrolyte body 11. Similarly, paired electrodes 21 and 22 are formed on opposite sides of the solid electrolyte body 13. Of these electrodes, the electrode 22 is sandwiched and buried between the solid electrolyte body 13 and the insulating substrate 24. Each of the solid electrolyte bodies 11 and 13, and the insulating substrates 12, 17, 18, and 24 is formed in the shape of an elongated plate, and FIG. 2 shows a cross section of the sensor element 10 taken perpendicular to the longitudinal direction thereof.

At one end of the insulating substrate 12 with respect to the longitudinal direction thereof, there is formed a hollow gas detection chamber 23, whose opposite wall surfaces are formed by corresponding surfaces of the solid electrolyte bodies 11 and 13 and into which the subject gas can be introduced. Porous diffusion-rate-limiting sections 15 are provided at opposite ends of the gas detection chamber 23 with respect to the width direction so as to limit the flow rate of the subject gas introduced into the gas detection chamber 23. The electrode 20 on the solid electrolyte body 11 and the electrode 21 on the solid electrolyte body 13 are exposed to the interior of the gas detection chamber 23.

Notably, a heat generation resistor 26 mainly formed of platinum is sandwiched and buried between the insulating substrates 18 and 17. The insulating substrates 17 and 18, and the heat generation resistor 26 function as a heater for heating the solid electrolyte bodies 11 and 13, to thereby activate them.

The surface of the electrode 19 on the solid electrolyte body 11 is covered with a porous protection layer 25 formed of ceramic (for example, alumina). That is, this protection layer 25 prevents the electrode 19 from deteriorating, which would otherwise be caused by poisoning components, such as silicon, contained in the exhaust gas. Furthermore, the insulating substrate 24 layered on the solid electrolyte body 11 has an opening so that the insulating substrate 24 does not cover the electrode 19, and the protection layer 25 is provided within the opening.

In the sensor element 10 having the above-described structure, the solid electrolyte body 11 and the pair of electrodes 19 and 20 provided on the opposite surfaces thereof function as an oxygen pump cell which pumps oxygen into the gas detection chamber 23 from the outside of the sensor element 10 or pumps oxygen out of the gas detection chamber 23 to the outside (in the following description, the solid electrolyte body 11 and the electrodes 19 and 20 will also be collectively referred to as an "Ip cell"). The solid electrolyte body 11 corresponds to the "second solid electrolyte body" of the present invention, and the pair of electrodes 19 and 20 correspond to the "pair of second electrodes" of the present invention.

The solid electrolyte body 13 and the pair of electrodes 21 and 22 provided on the opposite surfaces thereof function as an oxygen concentration detection cell which generates an electromotive force in accordance with an oxygen concentration between the electrodes (in the following description, the solid electrolyte body 13 and the electrodes 21 and 22 will also be collectively referred to as a "Vs cell"). The electrode 22 functions as an oxygen reference electrode which maintains an oxygen concentration which serves as a reference for detection of the oxygen concentration within the gas detection chamber 23. The solid electrolyte body 13 corresponds to the "first solid electrolyte body" of the present invention, and the pair of electrodes 21 and 22 correspond to the "pair of first electrodes" of the present invention. Notably, the specific functions of the Ip cell and the Vs cell will be described later.

Next, the configuration of the sensor control apparatus 3 connected to the sensor element 10 will be described. The sensor control apparatus 3 is mainly composed of a microcomputer 9 and an electric circuit section 30. The microcomputer 9 is a microcomputer chip on which a CPU 6 having a known configuration, ROM 7, RAM 8, etc. are mounted. Notably, the ROM 7 stores, for example, control programs for causing the CPU 6 to perform various types of processing, and a humidity correction table for performing humidity correction, which will be described later.

The electric circuit section 30 is composed of a heater energization control circuit 31, a pump current drive circuit 32, a voltage output circuit 33, a minute current supply circuit 34, a reference voltage comparison circuit 35, and pump current detection circuit 36.

The heater energization control circuit 31 supplies a voltage Vh to opposite ends of the heat generation resistor 26, while controlling the voltage through PWM, to thereby cause the heat generation resistor 26 to generate heat, thereby heating the Ip cell and the Vs cell. The minute current supply circuit 34 causes a very small current Icp to flow from the electrode 22 of the Vs cell to the electrode 21, to thereby move oxygen ions to the electrode 22, whereby an oxygen concentration atmosphere which serves as a reference is created. Thus, the electrode 22 functions as an oxygen reference electrode, which serves as a reference for detection of the oxygen concentration of the subject gas. The voltage output circuit 33 detects an electromotive force Vs produced between the electrodes 21 and 22 of the Vs cell. The reference voltage comparison circuit 35 compares a predetermined reference voltage with the electromotive force Vs detected by the voltage output circuit 33, and sends the comparison result to the pump current drive circuit 32 as feedback. The pump current drive circuit 32 controls the magnitude and direction of the pump current Ip flowing between the electrodes 19 and 20 of the Ip cell on the basis of the comparison result obtained from the reference voltage comparison circuit 35. Thus, the Ip cell pumps oxygen into the gas detection chamber 23 or pumps oxygen out of the gas detection chamber 23. The pump current detection circuit 36 converts the pump current Ip flowing between the electrodes 19 and 20 of the Ip cell to a voltage, and outputs the voltage to the microcomputer 9 as a detection signal.

In the present embodiment, two reference voltages (first and second reference voltages) are provided so as to be used as a reference voltage to be compared with the electromotive force Vs by the reference voltage comparison circuit 35. The first reference voltage is set to a voltage value (e.g., 450 mV) at which moisture ($H_2O$) contained in the subject gas introduced into the gas detection chamber 23 does not dissociate substantially when the oxygen concentration of the atmosphere within the gas detection chamber 23 is controlled, while the comparison result of the voltage output circuit 33 is fed back to the pump current drive circuit 32.

Meanwhile, the second reference voltage is set to a voltage value (e.g., 1000 mV) at which moisture ($H_2O$) contained in the subject gas introduced into the gas detection chamber 23 dissociates when the oxygen concentration of the atmosphere within the gas detection chamber 23 is controlled, while the comparison result of the voltage output circuit 33 is fed back to the pump current drive circuit 32.

In the above-described reference voltage comparison circuit 35, the first reference voltage is usually used as a reference voltage to be compared with the electromotive force Vs, and the oxygen concentration of the subject gas is calculated on the basis of the pump current Ip. Meanwhile, when humidity correction is performed for the full-range air-fuel-ratio sensor 1, the second reference voltage is used, as will be described in detail later. Notably, the pump current drive circuit 32, the voltage output circuit 33, and the reference voltage comparison circuit 35 correspond to the "current control means" of the present invention. The reference voltage which is compared with the electromotive force Vs corresponds to the "control target voltage" of the present invention, and the first and second reference voltages correspond to the "first voltage" and the "second voltage" of the present invention, respectively.

Next, the configuration of the ECU 5 will be described. The ECU 5 is an apparatus for electronically controlling, among others, drive of the engine 101 of the automobile. The ECU 5 uses a microcomputer chip on which a CPU having a known configuration, ROM, RAM, etc. are mounted. In the ECU 5, fuel injection timing and ignition timing are controlled through execution of control programs. As information for performing such control, an output (detection signal) corresponding to the oxygen concentration of the subject gas is input from the sensor control apparatus 3. Furthermore, signals from other sensors (for example, information regarding combustion pressure, cooling water temperature, and crank angle from which the rotational speed and piston position of the engine 101 can be detected) are input as other information.

Next, operation of detecting the oxygen concentration of the subject gas (the air-fuel ratio of exhaust gas) by use of the full-range air-fuel-ratio sensor 1 will be described briefly. Notably, when the oxygen concentration of the subject gas is detected, the first reference voltage (for example, 450 mV) is used for comparison by the reference voltage comparison circuit 35. As shown in FIG. 2, the minute current supply circuit 34 first causes a very small current Icp to flow from the electrode 22 of the Vs cell toward the electrode 21 thereof. As a result of this, oxygen contained in the subject gas is pumped from the electrode 21 side to the electrode 22 side via the solid electrolyte body 13, and the electrode 22 functions as an oxygen reference electrode. The voltage output circuit 33 detects the electromotive force Vs generated between the two electrodes 21 and 22. The reference voltage comparison circuit 35 compares the electromotive force Vs with the reference voltage. The pump current drive circuit 32 controls the magnitude and direction of the pump current Ip flowing between the electrodes 19 and 20 of the Ip cell on the basis of the result of the comparison by the reference voltage comparison circuit 35 such that the electromotive force Vs becomes equal to the reference voltage.

Notably, when the air-fuel ratio of the exhaust gas having flowed into the gas detection chamber 23 is on the rich side of a theoretical air-fuel ratio, since the oxygen concentration of the exhaust gas is low, the pump current Ip flowing between the electrodes 19 and 20 is controlled such that the Ip cell pumps oxygen into the gas detection chamber 23 from the outside. Meanwhile, when the air-fuel ratio of the exhaust gas having flowed into the gas detection chamber 23 is on the lean side of the theoretical air-fuel ratio, since a large amount of oxygen exists in the exhaust gas, the pump current Ip flowing between the electrodes 19 and 20 is controlled such that the Ip cell pumps oxygen out of the gas detection chamber 23 to the outside. The pump current Ip at that time is converted to a voltage by the pump current detection circuit 36, and the voltage is output to the ECU 5 as an output (detection signal) of the full-range air-fuel-ratio sensor 1. In the ECU 5, it is possible to determine the oxygen concentration of the subject gas (that is, the air-fuel ratio of the exhaust gas) on the basis of the magnitude and direction of the pump current Ip output from the full-range air-fuel-ratio sensor 1.

In the present embodiment, since the sensor unit 4 (the full-range air-fuel-ratio sensor 1 and the sensor control apparatus 3) has the same configuration as a conventional sensor unit, the sensor unit 4 is the same as the conventional sensor unit in terms of operation of detecting the oxygen concentration of the subject gas (the air-fuel ratio of exhaust gas). However, the sensor control apparatus 3 can detect not only the oxygen concentration of the subject gas (the air-fuel ratio of exhaust gas) but also the humidity of air introduced as the subject gas by use of the full-range air-fuel-ratio sensor 1. Thus, the sensor control apparatus 3 can correct the sensor output from the full-range air-fuel-ratio sensor 1 in accordance with the humidity of air, as will be described in detail later.

Figure 3:
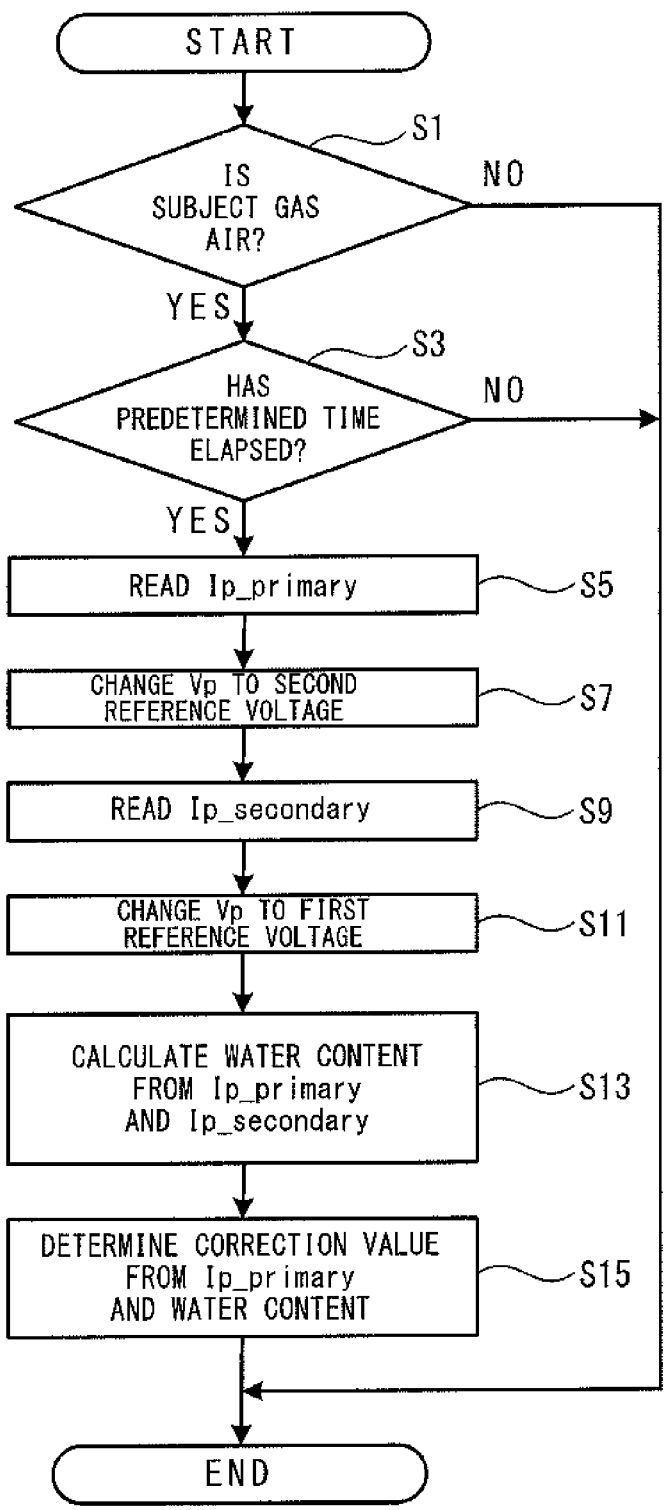
FIG. 3 Flowchart of main processing executed in a sensor control apparatus 3.

Next, main processing executed in the sensor control apparatus 3 will be described with reference to FIG. 3. A program for executing the processing shown in FIG. 3 is also stored in the above-described ROM 7 (see FIG. 2), and the CPU 6 (see FIG. 2) executes the program. This main processing is periodically executed at predetermined timings when the internal combustion engine system 100 is being operated. Notably, the processing for driving and controlling the heater energization control circuit 31, the pump current drive circuit 32, the voltage output circuit 33, the minute current supply circuit 34, the reference voltage comparison circuit 35, and the pump current detection circuit 36 of the electric circuit section 30 is executed separately from the main processing shown in FIG. 3. Notably, the sensor control apparatus 3 is configured such that, in a stage before the main processing shown in FIG. 3 is first executed after startup of the internal combustion engine, the reference voltage comparison circuit 35 uses the first reference voltage (e.g., 450 mV), and the pump current drive circuit 32 controls the supply of the Ip current to the Ip cell.

As shown in FIG. 3, when the main processing is started in the sensor control apparatus 3, the CPU 6 first determines whether or not the subject gas introduced into the full-range air-fuel-ratio sensor 1 is air (S1). In the present embodiment, the determination as to whether or not the subject gas is air is made on the basis of the result of a determination as to whether or not the microcomputer 9 (the CPU 6) receives a signal (hereinafter referred to as a "fuel cut signal") which indicates that fuel supply is being stopped in the internal combustion engine system 100. That is, the microcomputer 9 receives from the ECU 5, at predetermined intervals, the signal which indicates whether or not fuel supply is performed in the internal combustion engine system 100. In accordance with a separately executed program, the CPU 6 stores the received signal in the RAM 8. In S1, the CPU 6 determines whether or not it has received the fuel cut signal by determining whether or not the fuel cut signal is stored in the RAM 8 as the latest signal received from the ECU 5.

In the case where the fuel cut signal is received, fuel supply is being stopped in the internal combustion engine system 100. Therefore, air fills the exhaust passage of the exhaust pipe 102. That is, since the sensor element 10 is exposed to air, the CPU 6 determines that the subject gas is air (S1: YES). Notably, in a period during which the fuel cut signal is received continuously, a time clocked by an unillustrated timer is updated at predetermined intervals and is stored in the RAM 8 in accordance with a separately executed timer update program. Therefore, the time clocked by the timer represents the length of the period during which the fuel cut signal is continuously received; that is, a time elapsed after fuel supply has been stopped (i.e., fuel cut start time).

When the CPU 6 determines in S1 that the subject gas is air, the CPU 6 determines whether or not a predetermined time has elapsed from a point in time when fuel supply had been stopped in the internal combustion engine system 100. In the processing of S3, the CPU 6 determines whether or not the time clocked by the timer and stored in the RAM 8 is in excess of a predetermined time stored in the ROM 7. When the CPU 6 determines that the predetermined time has elapsed after the stoppage of fuel supply (S3: YES), air fills the exhaust passage of the exhaust pipe 102 sufficiently, and the sensor element 10 is surrounded by air whose oxygen concentration is known.

Next, the CPU 6 proceeds to S5 so as to read, via the pump current detection circuit 36, the pump current Ip flowing between the electrodes 19 and 20 of the Ip cell in a state where the reference voltage comparison circuit 35 uses the first reference voltage (e.g., 450 mV) (S5). The pump current Ip in this state will be referred to as "Ip_primary." The read "IP_primary" is stored in the RAM 8. Subsequently, the CPU 6 executes processing for changing the reference voltage used by the reference voltage comparison circuit 35 from the first reference voltage to the second reference voltage (e.g., 1000 mV) (S7).

Next, the CPU 6 proceeds to S9 so as to read, via the pump current detection circuit 36, the pump current Ip flowing between the electrodes 19 and 20 of the Ip cell in a state where the reference voltage comparison circuit 35 uses the second reference voltage (S9). The pump current Ip in this state will be referred to as "Ip_secondary." The read "IP_secondary" is stored in the RAM 8. Subsequently, the CPU 6 executes processing for changing the reference voltage used by the reference voltage comparison circuit 35 from the second reference voltage to the first reference voltage (S11).

Next, the CPU 6 calculates the water content of the subject gas from "Ip_primary" and "Ip_secondary" stored in the RAM 8 (S13). In S13, "Ip_primary" is subtracted from "Ip_secondary" so as to calculate a pump current difference, which represents the humidity-origin oxygen concentration of the subject gas (that is, the water content of the subject gas), and thus indicates the humidity of air introduced as the subject gas.

The CPU 6 then determines a correction value which represents an Ip current error $\Delta$Ip produced because of the air humidity, on the basis of the above-described "Ip_primary" and the water content calculated in S13 (S15). In a humidity correction table stored in the ROM 7 in advance, there are set Ip current errors $\Delta$Ip each corresponding to a combination of an Ip current indicated by "Ip_primary" and a water content of the subject gas. In S15, with reference to the humidity correction table of the ROM 7, the CPU 6 determines, as a correction value, an Ip current error ΔIp which corresponds to a combination of "Ip_primary" and the water content. The correction value determined in S15 is set in a predetermined storage area of the RAM 8.

Notably, preferably, "Ip_primary" used for calculation of the water content in S13 is read in S5, which is immediately before S7 in which the reference value used by the reference voltage comparison circuit 35 is changed from the first reference voltage to the second reference voltage. Thus, the time difference between the detection timing of "Ip_primary" and that of "Ip_secondary" can be reduced so as to suppress the occurrence of a problem in that the humidity changes between the detection of "Ip_primary" and the detection of "Ip_secondary."

The humidity correction table of the ROM 7 is set through performance of sampling of the output of the full-range air-fuel-ratio sensor 1 as described below. That is, in a state in which the full-range air-fuel-ratio sensor 1 is exposed to air under a given temperature condition, the pump current Ip output in accordance with the reference voltage being changed is detected, while only the humidity condition is varied. Notably, because of the individual difference of the full-range air-fuel-ratio sensor 1 in terms of performance, etc., the magnitude of the pump current Ip may vary among a plurality of such sensors even when the same reference voltage is used for control. Therefore, preferably, sampling of the output of the full-range air-fuel-ratio sensor 1 is performed for a plurality of full-range air-fuel-ratio sensors 1 which differ in pump current Ip output characteristics.

With reference to FIGS. 4 to 7, the results of the above-described sampling performed for the full-range air-fuel-ratio sensor 1 will be described. Notably, FIGS. 4 to 7 exemplify the results of sampling performed in such a manner that the pump current Ip output from the full-range air-fuel-ratio sensor 1 with the reference value being changed within a predetermined range was detected for the case where the full-range air-fuel-ratio sensor 1 was exposed to a given temperature condition ("25° C."), and the humidity (relative humidity) of air was changed among "20%," "50%," "80%," and "100%." Notably, when the humidity (relative humidity) of air is changed among "20%," "50%," "80%," and "100%," the water content (volume ratio) of air becomes "0.38%," "0.95%," "1.52%," and "1.89%," respectively.

Figure 4:
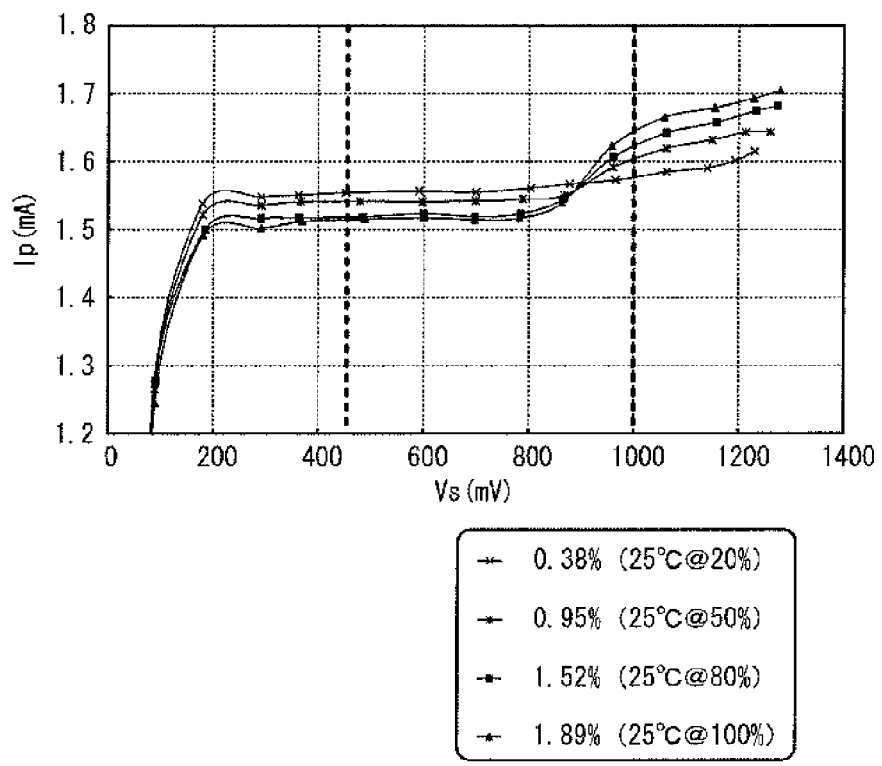
FIG. 4 Graph for describing the relation between reference voltage Vs and pump current Ip.
Figure 5:
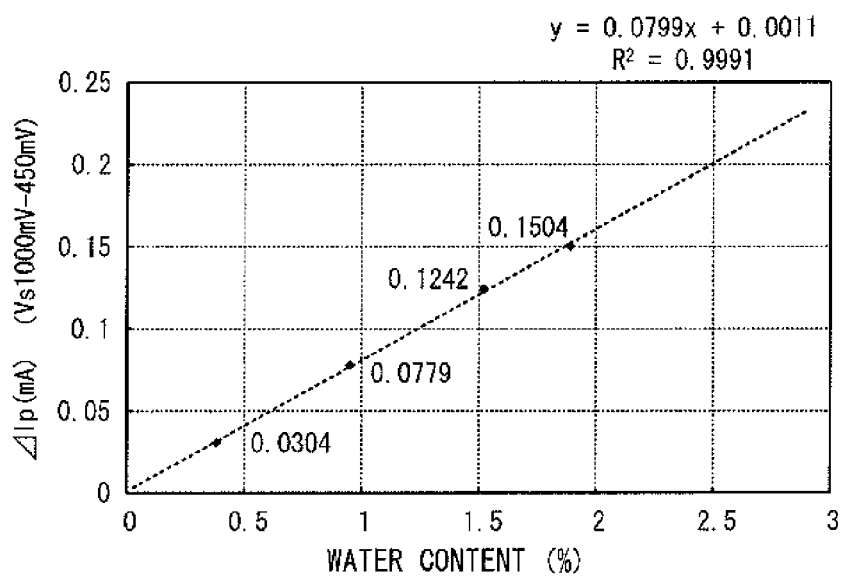
FIG. 5 Graph for describing the relation between water content of a subject gas and pump current error ΔIp.

For example, FIGS. 4 and 5 exemplify the results of the sampling performed for a full-range air-fuel-ratio sensor 1 having a relatively large Ip-current output tendency. As shown in FIG. 4, in the case of this full-range air-fuel-ratio sensor 1, when the reference voltage is increased from, for example, "80 mV," the pump current Ip increases as the reference voltage rises. When the reference voltage becomes greater than "200 mV," since oxygen contained in the subject gas can be moved sufficiently through the solid electrolyte body 13, the pump current Ip becomes substantially stable. When the reference voltage becomes greater than "900 mV," since oxygen can be dissociated, at the solid electrolyte body 13, from moisture contained in the subject gas, the pump current Ip increases. At that time, the higher the humidity, the greater the amount by which the pump current Ip increases. In other words, the lower the humidity, the smaller the amount by which the pump current Ip increases. When the reference voltage becomes greater than "1000 mV," since oxygen can be dissociated sufficiently, at the solid electrolyte body 13, from moisture contained in the subject gas.

With reference to the results of sampling of FIG. 4, an error ΔIp—which is the difference between the pump current Ip measured when the reference voltage is the first reference voltage (in the present embodiment, 450 mV) and the pump current Ip measured when the reference voltage is the second reference voltage (in the present embodiment, 1000 mV)—can be determined for each humidity condition; i.e., "20%" (water content: 0.38%), "50%" (water content: 0.95%), "80%" (water content: 1.52%), and "100%" (water content: 1.89%). As shown in FIG. 5, errors ΔIp of the pump current Ip under these humidity conditions are "0.0304 mA," "0.0779 mA," "0.1242 mA," and "0.1504 mA," respectively. As a result, when the water content (%) is represented by x (x-axis) and the pump current error ΔIp (mA) is represented by y (y-axis), the correlation between the water content and the pump current error ΔIp is represented by the following correlation function.

$$y=0.0799x+0.0011$$

At that time, the square of a correlation coefficient R (R-squared value) becomes as follows.

$$R^2=0.9991$$

Figure 6:
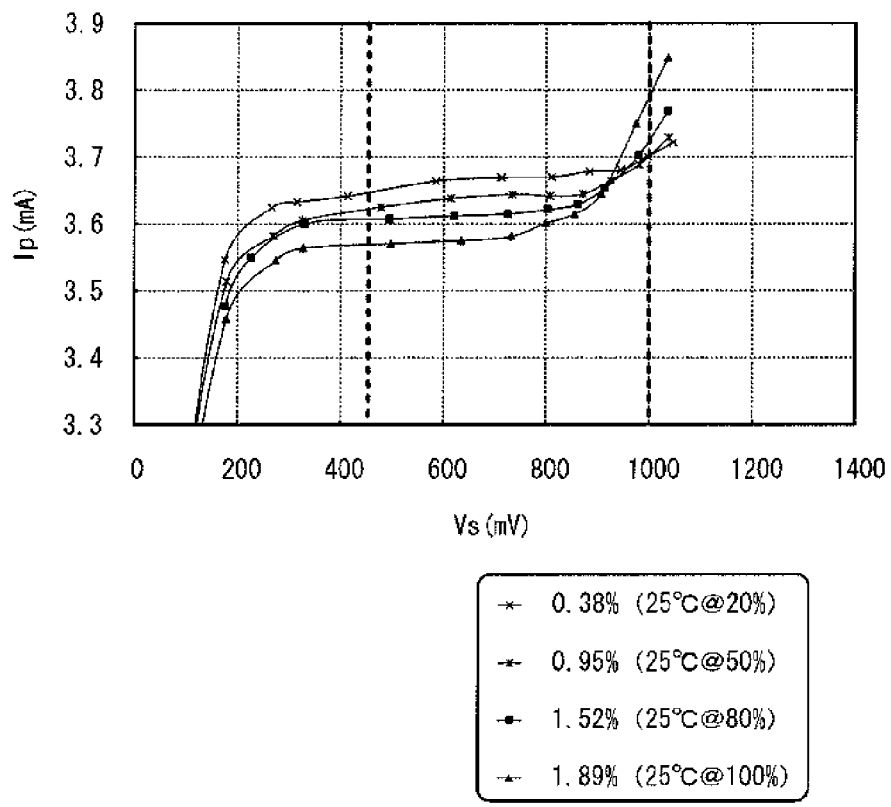
FIG. 6 Another graph for describing the relation between reference voltage Vs and pump current Ip.
Figure 7:
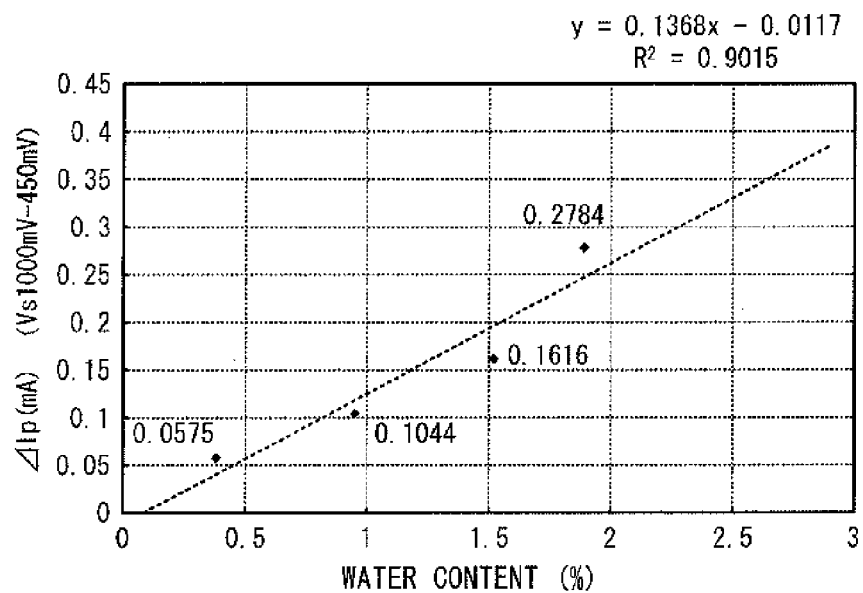
FIG. 7 Another graph for describing the relation between water content of a subject gas and pump current error ΔIp.
Figure 8:
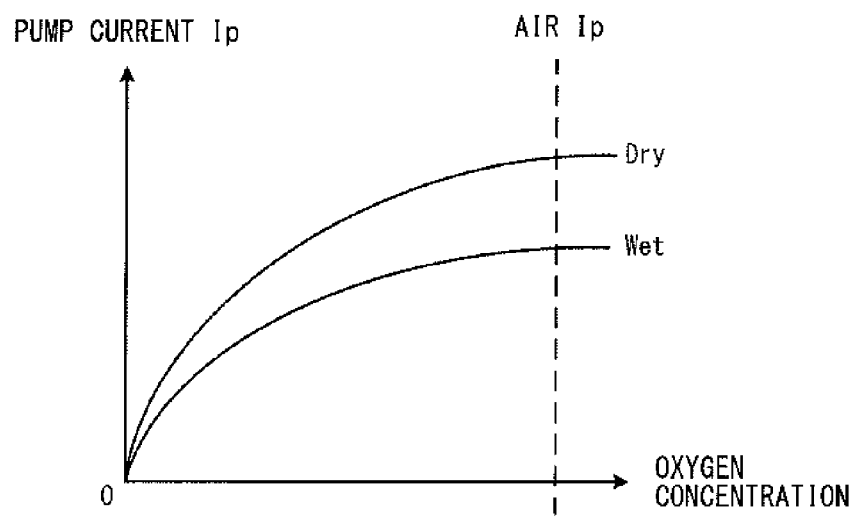
FIG. 8 Graph for describing the relation between oxygen concentration and pump current in a conventional oxygen sensor.
Figure 9:
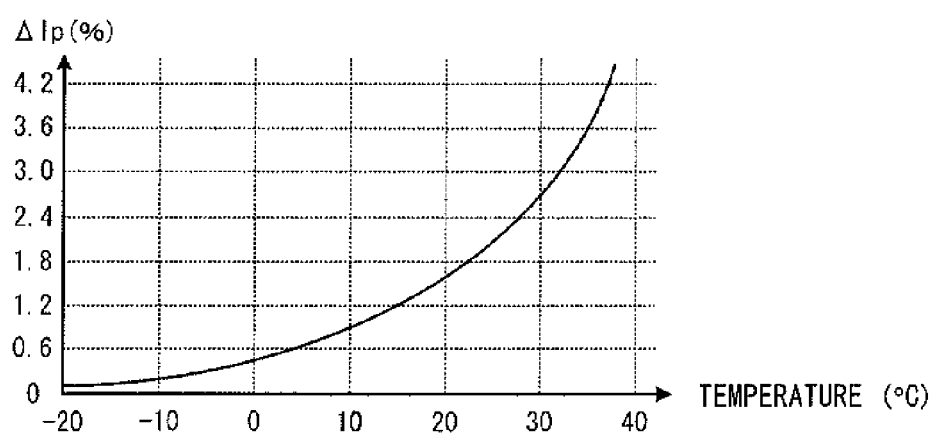
FIG. 9 Graph for describing the relation between humidity and pump current error ΔIp in the conventional oxygen sensor.

Meanwhile, FIGS. 6 and 7 exemplify the results of the sampling performed for a full-range air-fuel-ratio sensor 1 having a relatively small Ip-current output tendency. As shown in FIG. 6, in the case where the Ip-current output tendency is relatively small as well, a change in the pump current Ip with the magnitude of the reference voltage is the same as in the case where the Ip-current output tendency is relatively large (FIG. 4).

With reference to the results of sampling of FIG. 6, the error ΔIp—which is the difference between the pump current Ip measured when the reference voltage is the first reference voltage (in the present embodiment, 450 mV) and the pump current Ip measured when the reference voltage is the second reference voltage (in the present embodiment, 1000 mV)—can be determined for each humidity condition; i.e., "20%" (water content: 0.38%), "50%" (water content: 0.95%), "80%" (water content: 1.52%), and "100%" (water content: 1.89%). As shown in FIG. 7, errors ΔIp of the pump current Ip under these humidity conditions are "0.0575 mA," "0.1044 mA," "0.1616 mA," and "0.2784 mA," respectively. As a result, when the water content (%) is represented by x (x-axis) and the pump current error ΔIp (mA) is represented by y (y-axis), the correlation between the water content and the pump current error ΔIp is represented by the following correlation function.

$$y=0.1368x+0.0117$$

At that time, the square of a correlation coefficient R (R-squared value) becomes as follows.

$$R^2=0.9015$$

A pump current error ΔIp (that is, a correction value) for a combination of a value of the pump current Ip and a value of the water content of the subject gas is previously set in the humidity correction table of the ROM 7, on the basis of the results of the above-described sampling for the full-range air-fuel-ratio sensor 1. Notably, in place of the correction value, a correlation function corresponding to each value of the pump current Ip may be set in the humidity correction table. In this case, in the above-mentioned S15, a pump current error ΔIp corresponding to the water content calculated in S13 is calculated as a correction value on the basis of a correlation function corresponding to "Ip_primary."

Referring back to the main processing (FIG. 3), after the correction value is determined and set in a predetermined storage area of the RAM 8 in S15, the main processing (FIG.

3) is ended. Notably, in separate processing performed by the microcomputer 9 (CPU 6), the correction value set in the RAM 8 is used as a correction value (Ip current error ΔIp) for the pump current Ip detected via the pump current detection circuit 36 in a state in which the first reference voltage is used as the reference voltage for the reference voltage comparison circuit 35. Thus, once the correction value is determined in S15 of the main processing shown in FIG. 3, the pump current Ip separately detected by the microcomputer 9 (CPU 6) after that time is corrected by use of the correction value. Since the microcomputer 9 outputs the pump current Ip corrected by use of the correction value to the ECU 5 as an oxygen concentration detection signal, the ECU 5 can calculate an accurate oxygen concentration or air-fuel ratio, whereby precise air-fuel-ratio feedback control can be realized.

Notably, when the CPU 6 determines that the subject gas is not air in the processing of FIG. 3 (S1: NO), this means that fuel supply is being performed in the internal combustion engine system 100, and exhaust gas fills the exhaust passage of the exhaust pipe 102. When the CPU 6 determines that the predetermined period of time has not yet elapsed after stoppage of fuel supply (S3: NO), this means that fuel supply is started before air fills the exhaust passage of the exhaust pipe 102 sufficiently. In these cases, since the atmosphere around the sensor element 10 is not air, whose oxygen concentration is known, the CPU 6 ends the main processing in either case.

Incidentally, the CPU 6 which executes S1 in the main processing of the above-described embodiment (FIG. 3) corresponds to the "atmosphere determination means" of the present invention; the pump current detection circuit 36 and the CPU 6 which executes S5 correspond to the "first current detection mean" of the present invention; the CPU 6 which executes S7 and S11 corresponds to the "voltage setting means" of the present invention; the pump current detection circuit 36 and the CPU 6 which executes S9 correspond to the "second current detection mean" of the present invention; the CPU 6 which executes S13 corresponds to the "humidity detection mean" of the present invention; and the CPU 6 which executes S15 corresponds to the "correction value determination means" of the present invention. Furthermore, the microcomputer 9 which outputs the pump current Ip corrected by use of the correction value to the ECU 5 as an oxygen concentration detection signal, and the ECU 5 which calculate the oxygen concentration and/or air-fuel ratio on the basis of the detection signal correspond to the "gas concentration detection means" of the present invention.

Notably, the present invention is not limited to the embodiments described in detail above, and may be modified without departing from the scope of the present invention. Although the above-described embodiment exemplifies the case where the full-range air-fuel-ratio sensor 1 for detecting the oxygen concentration of the subject gas is used as a gas sensor for detecting the concentration of a specific component of the subject gas, the present invention is not limited thereto. For example, even when an NOx sensor is used for detecting the NOx concentration of the subject gas, humidity correction can be performed in the same manner as described above.

In the above-described embodiment, the determination as to whether or not the subject gas is air is performed on the basis of a fuel cut signal output when the supply of fuel to the internal combustion engine is stopped. However, the method of determining whether or not the subject gas is air is not limited thereto. For example, in the case where the full-range air-fuel-ratio sensor 1 has a device for charging into a space around the sensor element 10 a gas for correction whose oxygen concentration is known, the determination as to whether or not the subject gas is air may performed on the basis of a signal output when the gas for correction is charged.

In the above-described embodiment, the pump current Ip is output from the sensor control apparatus 3 to the ECU 5, and the ECU 5 determines the oxygen concentration of the subject gas (the air-fuel ratio of exhaust gas) on the basis of the pump current Ip. However, the present invention is not limited to such a configuration. For example, the embodiment may be modified such that the microcomputer 9 (CPU 6) of the sensor control apparatus 3 determines the oxygen concentration of the subject gas (the air-fuel ratio of exhaust gas) on the basis of the pump current Ip and the correction value determined in S15 shown in FIG. 3, and outputs the oxygen concentration or air-fuel ratio to the ECU 5. In this case, the microcomputer 9 which determines the oxygen concentration of the subject gas (the air-fuel ratio of exhaust gas) on the basis of the pump current Ip and the correction value determined in S15 shown in FIG. 3 corresponds to the "gas concentration detection means" of the present invention.

DESCRIPTION OF REFERENCE NUMERALS

1: full-range air-fuel-ratio sensor
3: sensor control apparatus
4: sensor unit
9: microcomputer
10: sensor element
11: solid electrolyte body
13: solid electrolyte body
23: gas detection chamber
32: pump current drive circuit
33: voltage output circuit
34: minute current supply circuit
35: reference voltage comparison circuit
36: pump current detection circuit
100: internal combustion engine system

The invention claimed is:

1. A gas-concentration/humidity detection apparatus including a gas sensor connected thereto and detecting concentration of a specific component of a subject gas and humidity of air introduced into the gas sensor as the subject gas, wherein the gas sensor comprises:

an oxygen concentration detection cell which includes a first solid electrolyte body and a pair of first electrodes formed on the first solid electrolyte body, one of the first electrodes being disposed within a detection chamber into which the subject gas is introduced, and the other first electrode being exposed to an oxygen concentration atmosphere serving as a reference; and an oxygen pump cell which includes a second solid electrolyte body and a pair of second electrodes formed on the second solid electrolyte body, one of the second electrodes being disposed within the detection chamber, and which pumps out oxygen contained in the subject gas introduced into the detection chamber or pumps oxygen into the detection chamber in accordance with current flowing between the pair of second electrodes, the gas-concentration/humidity detection apparatus being characterized by comprising:

current control means for detecting a voltage produced between the pair of first electrodes due to a difference between an oxygen concentration within the detection chamber and the oxygen concentration atmosphere that serves as a reference and for controlling the current flowing between the pair of second electrodes such that the voltage produced between the pair of first electrodes becomes equal to a control target voltage;

atmosphere determination means for determining whether or not the subject gas is air;

voltage setting means for setting the control target voltage to a first voltage and for setting the control target voltage to a second voltage greater than the first voltage when the atmosphere determination means determines that the subject gas is air;

first current detection means for detecting a first current which flows between the pair of second electrodes in a state in which the first voltage is produced between the pair of first electrodes;

second current detection means for detecting a second current which flows between the pair of second electrodes in a state in which the second voltage is produced between the pair of first electrodes; and humidity detection means for detecting humidity of the subject gas on the basis of the first current detected by the first current detection means when the atmosphere determination means determines that the subject gas is air, and the second current detected by the second current detection means after the first voltage is changed to the second voltage by the voltage setting means.

2. A gas-concentration/humidity detection apparatus according to claim 1, characterized by further comprising:

gas concentration detection means for detecting the concentration of the specific component on the basis of the first current detected by the first current detection means; and correction value determination means for determining a correction value, which is used for correcting the concentration detected by the gas concentration detection means, on the basis the humidity detected by the humidity detection means and the first current detected by the first current detection means when the atmosphere determination means determines that the subject gas is air.

3. A gas-concentration/humidity detection apparatus according to claim 1, characterized in that the humidity detection means obtains the humidity on the basis of a difference obtained by subtracting the first current from the second current.

4. A gas-concentration/humidity detection apparatus according to claim 1, characterized in that the humidity detection means detects the humidity on the basis of the first current detected by the first current detection means immediately before the control target voltage is set to the second voltage.

* * * * *